United States Patent
Ho et al.

(10) Patent No.: US 8,097,403 B2
(45) Date of Patent: Jan. 17, 2012

(54) FREEZE-DRIED PLATELETS, METHOD OF MAKING AND METHOD OF USE AS A DIAGNOSTIC AGENT

(75) Inventors: David Ho, McLean, VA (US); Heather Jones, Germantown, MD (US)

(73) Assignee: Cellphire, Inc., Rockville, MD (US)

( * ) Notice: Subject to any disclaimer, the term of this patent is extended or adjusted under 35 U.S.C. 154(b) by 1067 days.

(21) Appl. No.: 11/956,830

(22) Filed: Dec. 14, 2007

(65) Prior Publication Data

US 2008/0145834 A1    Jun. 19, 2008

Related U.S. Application Data

(60) Provisional application No. 60/869,915, filed on Dec. 14, 2006.

(51) Int. Cl.
  *A01N 1/02* (2006.01)
  *A01N 63/00* (2006.01)
  *G01N 33/86* (2006.01)
(52) U.S. Cl. ............................. 435/2; 424/93.72; 436/69
(58) Field of Classification Search .................. None
  See application file for complete search history.

(56) References Cited

U.S. PATENT DOCUMENTS

| | | | |
|---|---|---|---|
| 5,736,313 A | 4/1998 | Spargo et al. | |
| 5,993,804 A | 11/1999 | Read et al. | |
| 6,221,575 B1 | 4/2001 | Roser et al. | |
| 7,169,606 B2 | 1/2007 | DePablo et al. | |
| 2003/0022333 A1 | 1/2003 | Bronshtein | |
| 2005/0074402 A1 | 4/2005 | Cagnolini et al. | |

FOREIGN PATENT DOCUMENTS

| | | |
|---|---|---|
| WO | WO 01/58266 | 8/2001 |
| WO | WO 2004/050896 | 6/2004 |

OTHER PUBLICATIONS

Office Action, European Patent Application No. EP 05 78 4165; Jul. 2008.
Strong, D.M., Transfusion Medicine Bulletin, Vo. 2, No. 2, Jul. 1999.
Wolkers, W.F. et al., "Human Platelets Loaded with Trehalose Survive Freeze-Drying", *Cryobiology* 42:79-87, 2001.
Canadian Office action that issued with respect to patent family member Canadian Patent Application No. 2,577,068, mail date Jul. 4, 2011.

*Primary Examiner* — Sandra Saucier
(74) *Attorney, Agent, or Firm* — Greenblum & Bernstein, P.L.C.

(57) ABSTRACT

The present invention provides freeze-dried platelets and compositions comprising freeze-dried platelets for use as a diagnostic and calibration reagent for blood coagulation function. The invention also provides methods of diagnosing or monitoring blood coagulation function, including diagnosing or monitoring blood coagulation diseases and disorders. Kits for performing the methods of the invention are also included.

19 Claims, 5 Drawing Sheets

FREEZE-DRIED PLATELETS, METHOD OF MAKING AND METHOD OF USE AS A DIAGNOSTIC AGENT

CROSS-REFERENCE TO RELATED APPLICATIONS

This application relies on the disclosure of and claims the benefit of the filing date of U.S. provisional patent application No. 60/869,915, filed on 14 Dec. 2006, the entire disclosure of which is hereby incorporated herein by reference.

BACKGROUND OF THE INVENTION

1. Field of the Invention

The present invention relates to the field of medicine. More specifically, it relates to blood and blood products, and uses of those products to identify diseases and disorders affecting the blood or components of it. In many instances, the present invention relates to the field of dry platelet preparations and their use in diagnosis and monitoring of diseases and disorders relating to platelet function.

2. Description of Related Art

Platelets are formed in the bone marrow as fragments of megakaryocytes. They are irregularly-shaped, colorless bodies that are present in blood at a concentration of 150,000-450,000 per microliter (ul). Platelets play a crucial role in normal hemostasis, and they are the first line of defense against blood escaping from injured blood vessels. When bleeding from a wound suddenly occurs, the platelets gather at the wound and attempt to block the blood flow by forming a clot. The sticky platelets adhere to the damaged area and gradually form a platelet plug. At the same time, the platelets release a series of chemical signals that prompt other factors in the blood to reinforce the platelet plug. Between the platelet and its reinforcements, a sturdy clot is created that acts as a patch while the damaged area heals.

Blood clotting is a complicated process: if the clot formation is unchecked, the vessel will become occluded; if the clot is not sturdy, excessive blood loss will occur. Therefore, a delicate balance must be maintained for normal hemostasis. In situations where normal hemostasis is unbalanced, clot formation may be compromised. Such an abnormality could be acquired due to ingestion of aspirin or caused by immune dysfunction. The abnormality could also be congenital, such as through genetic diseases and clotting factor defects. For example, defects in the process of hemostasis that lead to bleeding disorders have been identified, and most of such defects are in the enzymes involved in the cascade of activities required for clotting, in platelet activation and function, or in contact activation. Included among these disorders are von Willebrand's Disease (vWD) and hemophilia. Other diseases or disorders of the blood clotting system are a result (i.e., side effect) of treatments for other diseases or disorders. Treatments for such diseases and disorders typically involve reducing the dose of the drug causing the side effect, or discontinuing treatment with the drug.

Typically, detection of a blood clotting disease or disorder involves analyzing the patient's blood for platelet counts, various markers involved in blood clotting, and clot-forming ability. The coagulation assays measuring the activated clotting time (ACT), the prothrombin time (PT), the plasma thrombin time (PTT), and the activated partial thromboplatin time (APTT) are used to evaluate the intrinsic and extrinsic coagulation pathways. These assays are generally performed in the laboratory and analysis often requires multiple samples of blood to be drawn from the patients. Moreover, these assays are potentially unreliable as they are end-point tests in which results are based on the time of clot formation in vitro. Another limitation relates to the fact that exogenous reagents, such as kaolin, thrombin, calcium, etc. must be added; thus, the results are based on an artificial system, and do not necessarily reflect the patient's thrombotic potential.

Platelet functionality is another critical component of blood clots. Dysfunctional platelets can lead to abnormal hemorrhage, such as bleeding or thrombosis. Thus, platelet function assays are an integral part of the diagnosis and monitoring of blood related diseases. For example, acquired platelet defects, such as ingestion of aspirin, cardiac disease, renal disease, or congenital platelet defects such as Bernard-Soulier syndrome, Glanzmann's thrombasthenia and storage pool disease, to name a few, can influence the normal hemostatic function of the platelets. To assess the platelet function, at the very minimal, a complete blood count with a peripheral blood smear will provide some basic information. Other tests, such as bleeding time, platelet function tests using an aggregometer to assess the aggregation of platelets to a panel of platelet agonists performed on whole blood or platelet rich plasma, will classify the defect. However, such analyses, although accurate, are not highly sensitive, and can fail to detect slight perturbations in normal clotting function at early stages of a disorder. Likewise, determination of the precise point of failure of the blood clotting cascade may require numerous assays using freshly drawn blood.

One proposal for use of platelets as hemostatic agents and in diagnostics is to prepare platelets in a freeze-dried state and store them for later use. Many groups have attempted to produce suitable freeze-dried platelets for various uses. For example, U.S. Pat. No. 5,622,867 to Livesey et al. discloses a system for cryoprotecting platelets for storage. The system treats fresh platelets with an inhibitor system comprising second messenger effectors. Inhibitors of one or more of the following pathways are added: cAMP, sodium channel, cGMP, cyclooxygenase, lipoxygenase, phospholipase, calcium, proteinase and proteinase, and membrane modification. A cryoprotectant, such as dimethyl sulfoxide (DMSO), maltodextrin, dextran, hydroxyethyl starch, and glucose, is also added where the platelets are to be maintained at low temperatures. Prior to use, the platelets are washed to remove the inhibitors and cryoprotectant.

In addition, U.S. Pat. No. 5,656,498 to Iijima et al. discloses freeze-dried platelets and methods of making them. The method comprises pre-treating platelets in blood plasma with a solution containing a saccharide, a biopolymer, an acid, or an acid salt, granulating the treated plasma, rapidly cooling the granules, and freeze-drying the granules. Furthermore, U.S. Pat. No. 5,736,313 to Spargo et al. discloses freeze-dried platelets and a process for making them. The process of making the freeze-dried platelets according to that patent comprises pre-incubating the platelets in a phosphate-citrate buffer or a phosphate-phosphate-citrate buffer, both of which contain a carbohydrate (e.g., glucose). After pre-incubation, the platelets are loaded with a carbohydrate, then suspended in a lyophilization buffer containing a matrix-forming polymer and a carbohydrate. The platelets are then slowly cooled to about −50° C. while the pressure is reduced to a vacuum state.

U.S. Pat. Nos. 5,958,670 and 5,800,978, both to Goodrich et al., also disclose freeze-dried platelets and methods of making them. The inventions disclosed in these patents rely on use of compositions having glass transition temperatures of above about −60° C. The compositions generally comprise a component that is permeable to the platelets (e.g., a carbohydrate, such as a sugar) and a component that is impermeable to the platelets (e.g., gelatin, PEG). To create the freeze-dried platelets, the temperature of the composition is reduced to a point below the glass transition temperature of the composition, and vacuum evaporating or subliming the liquid from the composition. An earlier patent, U.S. Pat. No. 5,213,814, also to Goodrich et al., discloses stabilized platelets and methods of making them. The methods and platelets are suitable for storage of the platelets for extended periods of time at about 4° C. The methods generally comprise immersing platelets in a buffered aqueous solution containing a carbohydrate and a biologically compatible polymer or mixture of polymers, then freezing the solution and drying the frozen solution to produce freeze-dried platelets containing less than 10% by weight of moisture.

U.S. Pat. Nos. 6,127,111 and 6,372,423, both to Braun, disclose freeze-dried platelets and methods of making them. The methods of making the freeze-dried platelets comprise exposing the platelets to a coagulation inhibitor (e.g., EDTA or citrate) and a "cake forming agent" (e.g., a protein such as serum albumin, or a polysaccharide such as mannitol) for about 5 to 60 minutes at room temperature, and then freeze-drying to reduce the moisture content to below 10%.

Investigators at the University of California, Davis, have developed a process for making freeze-dried platelets which comprises loading the platelets with trehalose prior to freeze-drying. In U.S. Pat. No. 6,723,497, a method of preparing freeze-dried platelets is disclosed in which platelets are loaded with trehalose by incubating the platelets at a temperature from about 25° C. to less than about 40° C. with up to 50 mM trehalose, cooling the loaded platelets to below −32° C., and lyophilizing the cooled platelets. Published U.S. patent application 2005/0048460 discloses a method for making freeze-dried platelets that includes exposing the platelets to a carbohydrate (e.g., trehalose) and an amphiphilic agent (e.g., arbutin), and freeze-drying the platelets. Other patents and patent application publications relating to this field include, for example, U.S. Pat. Nos. 6,770,478, 6,723,497, 5,827,741, and U.S. published patent applications numbers 2005/0048460, 2004/0152964, 2004/0147024, and 2004/0136974.

U.S. Pat. No. 6,833,236 to Stienstra discloses a method for the production of stabilized platelets, and platelets made by the method. The method comprises pre-activating the platelets, for example by exposing them to stress, to induce formation of microvesicles, contacting the pre-activated platelets with a carbohydrate to introduce the carbohydrate into the platelets, and drying the loaded platelets.

The inventors and their colleagues have likewise developed freeze-dried platelets, compositions containing them, and methods of making them. Their inventions are disclosed, for example, in U.S. patent application Ser. Nos. 11/197,310 and 11/152,774, and in international patent application PCT/US2005/028559. An exemplary method disclosed in one or more of these patent documents includes loading platelets with 100 mM trehalose in the presence of 1% ethanol. The method also includes addition of 6% (final concentration) of polysucrose 400 as a stabilizing matrix before lyophilization.

Although numerous groups have developed processes for making freeze-dried platelets, and even though numerous advances in detecting and treating bleeding disorders have taken place over the last several years, the inventors have recognized that there is still a need for improved compositions and methods for detecting such disorders, particularly more sensitive and accurate methods to detect the development of the disorders.

SUMMARY OF THE INVENTION

The present invention provides freeze-dried platelets, compositions comprising them, methods of making them, kits comprising them, and methods of using them. In general, the methods of making the freeze-dried platelets of the invention comprise obtaining fresh platelets from blood or a blood product, incubating the platelets in the presence of an aprotic solvent, exposing the platelets to a polysaccharide, exposing the platelets to a cryoprecipitate or a fraction thereof, and lyophilizing the platelets. Optionally, the platelets can be isolated by centrifugation and can be resuspended in a loading buffer before exposure to a polysaccharide. Also optionally, the freeze-dried platelets can be reconstituted with a liquid. In a preferred embodiment, the platelets are incubated in the presence of DMSO, an aprotic solvent.

In one aspect, the invention provides freeze-dried platelets. In general, the freeze-dried platelets of the present invention have all or essentially all of the surface markers that are known to be relevant to blood clotting and that are present on platelets found in vivo or on freshly obtained platelets. In contrast to other freeze-dried platelets known in the art, the freeze-dried platelets of the present invention have the ability to rapidly respond to normal platelet agonists. For example, they can rapidly respond to agonists currently being used to assess platelet activation functions, such as thrombin, thrombin activation peptide (TRAP), arachidonic acid, collagen, ADP, ristocitin, and epinephrine. Thus, they can be considered to have superior responses to agonists, as compared to freeze-dried platelets known in the art. In addition, as compared to freeze-dried platelets known in the art, the freeze-dried platelets of the present invention quickly produce, upon exposure to one or more agonists, aggregates of a size sufficient to detect using standard light transmission aggregometry. Like the compositions discussed below, the platelets of the invention can be used as a control reagent for test methods that are currently in use for testing the activity of blood and blood components. They also can be used as a control reagent for calibrating instruments, such as light transmission aggregometers.

In another aspect, the present invention provides compositions comprising platelets. The platelets can be freeze-dried, reconstituted from freeze-dried platelets, or fresh. The compositions can, but do not necessarily, comprise microparticles in addition to the platelets. Likewise, the compositions may comprise a liquid solvent, such as water or another biologically tolerable substance. In embodiments, the compositions comprise some or all of the substances used to prepare freeze-dried platelets according to the present invention. The compositions can be used to diagnose a disorder of the blood clotting system. They likewise can be used to monitor the blood clotting ability of a patient's blood clotting system over a period of time, such as, for example, during a treatment regimen for a disease or disorder of the blood clotting system or another system or tissue within the patient's body. In some embodiments, the platelets are used as a control or a calibration reagent for aggregation of platelets in test samples.

In a further aspect, the invention provides a method of making the freeze-dried platelets and compositions of the invention. In general, the method comprises obtaining platelets and freeze-drying them using a process that includes incubation in the presence of DMSO and exposure to cryoprecipitate prior to lyophilization. As used herein, cryoprecipitate is a blood product prepared from plasma in which each 15 ml unit contains about 100 U of Factor VIII, at least 150 mg of fibrinogen (often at least 350 mg), von Willebrand factor, Factor XIII, and fibronectin. The freeze-dried platelets and compositions comprising them can be stored for extended periods of time prior to use, and retain essentially all of their blood clotting functions during storage and through reconstitution. While the compositions of the invention typically are dry compositions, in embodiments, the compositions comprise water or another biologically tolerable solvent. Accordingly, in embodiments of making the freeze dried platelets and compositions, the method comprises reconstituting the freeze dried platelets with a liquid. The freeze-dried platelets and compositions according to the present invention are useful for diagnosing various diseases and disorders of the blood clotting system, and as control reagents for clotting reactions. They are particularly useful in in vitro settings, such as in diagnostic reactions. The platelets of the compositions may be indated (freshly isolated) or outdated (older than permitted by FDA regulations for therapeutic uses of blood).

In yet another aspect, the present invention provides a method of diagnosing a disease or disorder of the blood clotting system. The method generally comprises combining freeze-dried platelets of the invention with platelets and/or plasma removed from a patient having, or suspected of having, a disease or disorder of the blood clotting system to form a mixture, and determining whether the person has a defect in the blood clotting system by assaying one or more biological or biochemical functions of the mixture, where the defect decreases or abolishes the patient's blood clotting system's ability to function normally or to cause clot formation in a pre-defined period of time. Typically, determining whether the patient's blood clotting system is defective comprises assaying clotting time of the mixture.

In an additional aspect, the invention provides a method of monitoring the progression of a disease or disorder of the blood clotting system. The method generally comprises combining freeze-dried platelets of the invention with platelets and/or plasma removed from the patient suffering from the disease or disorder to make a mixture, and determining the blood clotting ability of the mixture. Typically, determining the blood clotting ability of the mixture indicates the blood clotting ability of the patient's blood, and comprises assaying clotting time of the mixture. Furthermore, typically, multiple assays are performed over time to give an indication of progression over time.

In another aspect, the invention provides a method of monitoring the effects of a treatment regimen for a patient on the blood clotting system of that patient. In general, the method comprises combining freeze-dried platelets of the invention with platelets and/or plasma removed from the patient undergoing the treatment regimen to make a mixture, and determining the blood clotting ability of the mixture. Typically, determining the blood clotting ability of the mixture indicates the blood clotting ability of the patient's blood, and comprises assaying clotting time of the mixture. Furthermore, typically, multiple assays are performed over time to give an indication of the effects of the treatment regimen over time.

An aspect of the invention is directed to a kit for performing a method of the invention. Typically, the kit of the invention comprises freeze-dried platelets of the invention. The kit can also comprise some or all of the other reagents and supplies necessary to perform at least one embodiment of one method of the invention. Thus, the kit can be a diagnostic kit, a blood clotting monitoring kit for coagulation proteins or platelets, or a drug treatment monitoring kit. Often, the kit will comprise some or all of the supplies and reagents needed to perform one or more control reactions to ensure the kit is performing properly and to provide baseline results against which test samples can be compared.

BRIEF DESCRIPTION OF THE DRAWINGS

The accompanying drawings, which are incorporated in and constitute a part of this specification, illustrate data supporting embodiments of the invention, and together with the written description, serve to explain certain principles and concepts of the invention.

DETAILED DESCRIPTION OF VARIOUS EMBODIMENTS OF THE INVENTION

Figure 1:
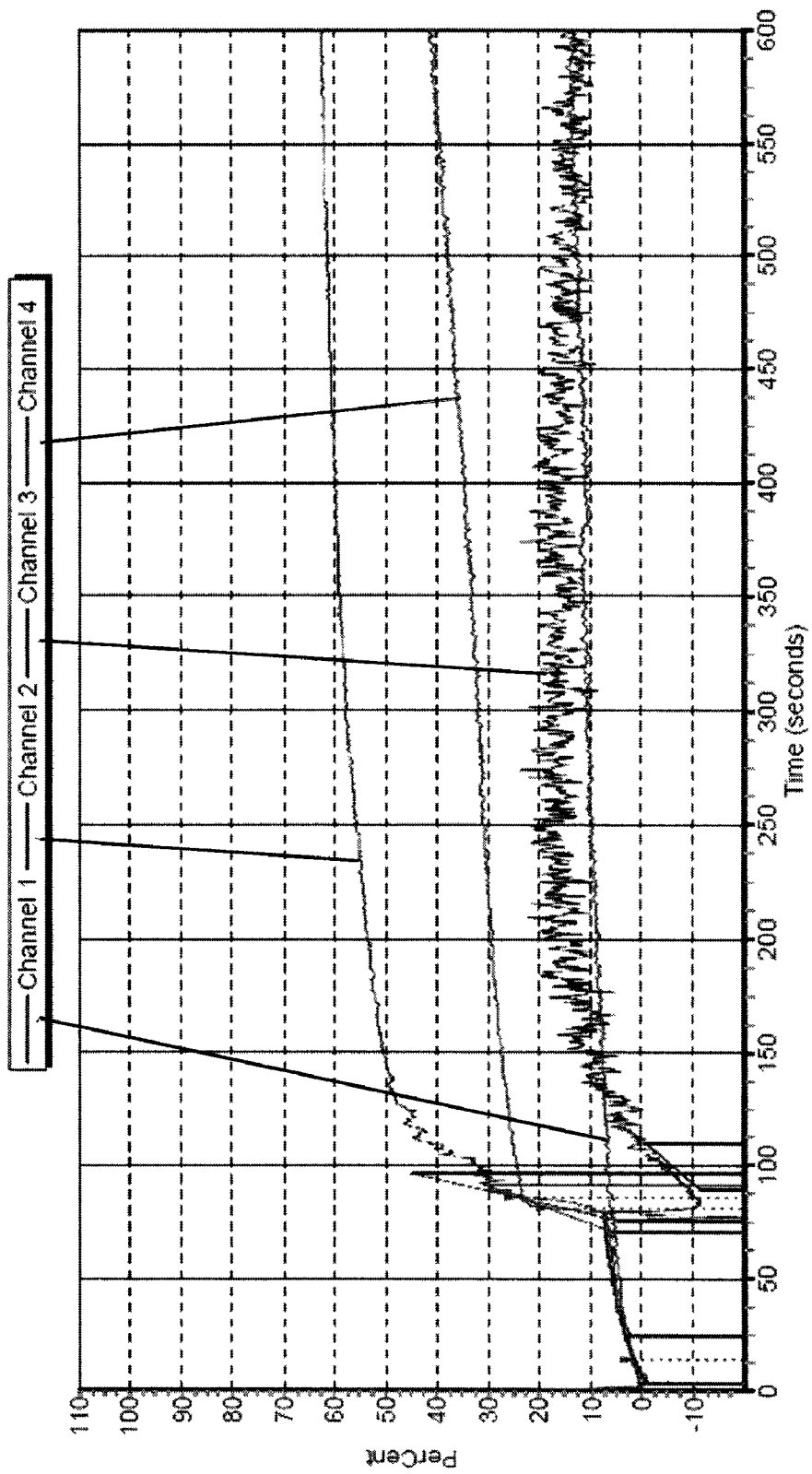
FIG. 1 is a graph depicting the reaction of freeze-dried platelets of the present invention with various agonists.

Reference will now be made in detail to various exemplary embodiments of the invention. The following detailed description is provided to describe in detail certain aspects and embodiments of the invention. It should not be construed as limiting the invention to the particular described aspects, embodiments, or features. Rather, it should be understood as providing details on certain parts of the invention to give the reader a better understanding of various concepts encompassed by the invention, which can be applied to numerous embodiments, both particularly disclosed and evident from the description.

The present invention is based, at least in part, on the usefulness of freeze-dried platelets for all diagnostic capabilities provided by fresh platelets, including monitoring any and all functions of platelets. It thus recognizes the usefulness of freeze-dried platelets in monitoring the blood clotting ability of an individual's blood, including when that person has a blood clotting disorder that is either natural or induced by a treatment regimen for treatment of a disease or disorder affecting the individual. In view of the improved platelet function of the freeze-dried platelets according to the present invention over those known in the art, the freeze-dried platelets and compositions comprising them can be used as standards or controls for assays of blood or blood fractions, and for calibrating instruments that are used to detect blood coagulation ability and other functions of blood involving platelets.

Accordingly, in one aspect, the invention provides freeze-dried platelets and reconstituted platelets obtained by rehydration of the freeze-dried platelets. In a preferred embodiment, the freeze-dried platelets are made by a process comprising obtaining fresh platelets from blood or a blood product, incubating the platelets in the presence of an aprotic solvent, exposing the platelets to a polysaccharide, exposing the platelets to a cryoprecipitate or a fraction thereof, and lyophilizing the platelets. Optionally, the freeze-dried platelets can be isolated by centrifugation and resuspended in a loading buffer before being exposed to a polysaccharide. Also, optionally, the freeze-dried platelets can be reconstituted with a liquid. Tests performed by the inventors have shown that the freeze-dried platelets of the present invention have all or essentially all of the surface markers that are known to be relevant to blood clotting and that are present on platelets found in vivo or on freshly obtained platelets. For example, a sample of the freeze-dried platelets of the present invention shows the following markers to be present on platelets in the sample: GPIIb-IIIa, GPIb, P-selectin, and charged lipids such as PC/PS.

One particularly advantageous characteristic of the freeze-dried platelets of the present invention is their ability, upon rehydration, to rapidly respond to certain platelet agonists. For example, the range for freeze-dried platelets of the invention can be 1-5 minutes for arachidonic acids, collagen and thrombin, which is the same range seen for fresh platelets, although for both, the reaction normally occurs within the first minute. Freeze-dried platelets known in the art usually do not respond, but if they do, it usually requires 5 minutes or more, and can take as long as 10 minutes. Thus, while perhaps not absolutely identical to fresh platelets in their functional responses, the freeze-dried platelets of the present invention can be considered to have superior responses to agonists, as compared to freeze-dried platelets known in the art.

In addition, as compared to freeze-dried platelets known in the art, the freeze-dried platelets of the present invention quickly produce, upon exposure to one or more agonists, aggregates of a size sufficient to detect using standard light transmission aggregometry. Use of the present freeze-dried platelets in detection instruments currently on the market is thus superior to prior art freeze-dried platelets, and provides advantages over those platelets. These advantages include both the adequate size of aggregates in the present invention so that they can be detected in standard instruments and the rapidity of formation of the aggregates, thereby allowing quicker detection.

Like the compositions discussed below, the platelets of the invention can be used as a control reagent for test methods that are currently in use for testing the activity of blood and blood components. They also can be used as a control reagent for calibrating instruments, such as light transmission aggregometers, clot instruments, platelet function analyzers, and thromboelastograms.

In another aspect, the present invention provides compositions comprising the platelets of the invention. The compositions may comprise platelets that are freeze-dried or reconstituted from freeze-dried platelets, along with one or more other substances, the identities of which are not particularly limited. As a general matter, the other substance(s) need only be limited by their ability to be compatible with functional platelets in an environment in which the platelets will be assayed for activity. Thus, in general, the substance(s) may be any substance(s) that do not interfere with an assayable platelet function. In many embodiments the compositions comprise microparticles in addition to the platelets. In some embodiments, the compositions comprise a liquid solvent, such as water or another biologically tolerable substance. Water-based buffers are particularly well suited as substances to be included in a composition of the invention, particularly where the composition is to be used in an assay for platelet function. In certain particular embodiments, the compositions comprise water or saline, such as phosphate-buffered saline. For in vitro applications, the composition may comprise one or more substance that is toxic or otherwise could be harmful to a living organism. Although in vivo use of the present freeze-dried platelets is not a preferred use, where the platelets are used in vivo (e.g., for topical treatment of bleeding), the compositions should not comprise substances that are toxic or otherwise harmful to the subject (e.g., human or animal) being treated.

As mentioned above, the compositions may be lyophilized platelets. The compositions thus may be dry compositions, in which the moisture content is 10% or less, such as 5% or less, 1% or less, or 0.5% or less. Preferably, the moisture content is 5% or less, such as 2% or less.

In embodiments, the compositions comprise some or all of the substances used to prepare freeze-dried platelets according to the present invention. The compositions thus may comprise one or more salts, such as phosphate salts, sodium salts, potassium salts, calcium salts, magnesium salts, and any other salt that can be found in blood or blood products, or that is known to be useful in freeze-drying platelets or eukaryotic cells, or any combination of two or more of these. In addition or alternatively, the composition may comprise one or more sugars or polysugars, such as monosaccharides and disaccharides (e.g., maltose, dextrose, mannose, trehalose, sucrose, polymers of sucrose, glucose), and polysaccharides, such as polysucrose. Likewise, the composition may additionally or alternatively comprise one or more chelating agents, one or more cryoprotectants (e.g., DMSO), or one or more components of cryoprecipitate (e.g., fibrinogen). Yet other exemplary substances include biological molecules derived from human or animal sources, such as albumin, casein, laminin, fibrinogen, and the like. Of course, because the freeze-drying procedure can result in lysis of a certain number of platelets, compositions of the invention may comprise, external to intact platelets, some or all of the components present in the interior of a platelet. Other non-limiting exemplary substances include glycerol, triglycerides, lipids, and the like. The compositions may comprise one or more substances, combinations of two or more substances, and/or metabolic or chemical break-down products of one or more substances, including but not limited to those mentioned herein.

Substances that may be present in a composition of the invention include chemical and biological compounds that function as drugs. Yet other substances include substances that function as food. In addition, other substances include substances that function as herbal supplements. In embodiments, the composition comprises one or more anti-coagulants. As will be discussed below in more detail, the compositions and methods of the present invention are particularly well suited for detection and monitoring of drugs, food, and herbal supplements in blood samples, and detection and monitoring of the effects of these substances on the blood clotting system of the patient to whom the drugs, etc. are administered. Among the drugs are Warafin (Coumadin®), Heparin, Clopidogrel (Plavix®), Dipyridamole (Persantine®), Enoxaparin (Lovenox®), Ardeparin (Normiflo®), Dalteparin (Fragmin®), Ticlopidine (Ticlid®), Danaparoid (Orgaran®), Tinzaparin (Innohep®), Aspirin, Thrombin Inhibitors, and the like. Also among the substances are certain food and herbal supplements that contain coumarins with potential anticoagulant effects, such as Alfalfa, Angelica (Don Quai), Arnica, Bogbean, Capsicum, Celery, Dandelion, Horse chestnut, Horseradish, Meadowsweet, Nettle, Parsley, Passion, Flower, Red Clover, Sweet Clover, Wild Carrot, Wild Lettuce. In addition, the substances can be those that have anti-platelet properties, such as Agrimony, Aloe gel, Black cohosh, Bogbean, Clove, Dandelion, Garlic, Ginger, Ginkgo biloba, Ginseng (Panax), Licorice, Meadowsweet, Onion, Policosanol, Poplar, Senega, Tamarind, Willow Wintergreen, and the like.

Re-hydrated platelets according to the invention comprise freeze-dried platelets that have been reconstituted by exposure to water or an aqueous solution, such as a water-based buffer (e.g., phosphate buffered saline). Reconstitution may be by any method known in the art, such as immersion in water or slow re-hydration with water vapor. Re-hydrated freeze-dried platelets according to the invention will typically be in a composition that comprises water, although other solvents may be used or included with the water. The identity of the solvent is not particularly limited, with the main restriction being that the solvent cannot be present in an amount that interferes with normal function of the platelets. As with reconstituted platelets in a purified state, the compositions that comprise the reconstituted platelets of the invention include platelets that are activated to some degree. Unlike some prior technologies for producing freeze-dried platelets, which produces inactive platelets, and other technologies that produces totally or nearly totally activated platelets, the present invention provides reconstituted platelets and compositions comprising them in which the platelets are only slightly activated, and still have the ability to aggregate.

As is the case with the platelets of the invention, compositions comprising the present freeze-dried platelets or reconstituted freeze-dried platelets can be used for many applications, both in vitro and in vivo. The use is not particularly limited, and may be any use those of skill in the art can envision for platelets. Where used for diagnostic purposes, the compositions may be used to diagnose a disorder of the blood clotting system of a subject, which can be a naturally-occurring disorder or one that is induced as a result of treatment of the subject for another disorder or disease. For example, the compositions can be used to determine if a subject has a bleeding disorder resulting from a genetic defect in the production of platelets or one or more receptors naturally found on a normally functioning platelet. They likewise can be used to monitor the blood clotting ability of a patient's blood clotting system over a period of time, such as, for example, during a treatment regimen for a disease or disorder of the blood clotting system or another system or tissue within the patient's body. Thus, for example, the platelet-containing compositions of the invention may be used to monitor the blood clotting ability of patients being treated for high blood pressure, coronary disease, or hypertension. They also may be used to monitor the blood clotting ability of patients being prepared for surgery. The compositions thus may be used to monitor the blood of patients being treated with any one or more of the drugs or compounds listed above.

In some embodiments, the platelets and/or compositions of the invention are used as a control or a calibration reagent for aggregation of platelets in test samples. The freeze-dried platelets of the present invention may be stored in a stable state for extended periods of time. They thus may be used to repeatedly calibrate a detection instrument to ensure that successive readings for patient blood samples are comparable and accurate. More specifically, multiple aliquots of a sample of freeze-dried platelets may be made at one time and stored for future use. Each sample will have the same platelets and same activity upon reconstitution. Therefore, the samples may be assayed on a single machine over a period of time, with the expectation that the results provided by each aliquot will be identical or statistically the same as the prior aliquot. In this way, the instrument may be calibrated, and changes in the clotting ability of a patient's blood (or changes between one patient and another) may be detected with a high level of confidence.

The platelets that are present in compositions of the invention have essentially all of the gross morphological characteristics of normal, freshly obtained platelets in blood. For example, in certain compositions where freeze-dried platelets are present, about 70% of the particles in the composition are retained when the composition is filtered through a mesh size that retains particles of the size of a typical platelet. Likewise, generally the platelet particles show the same array of cell surface proteins as fresh, untreated platelets. For example, size, granularity, and surface receptors, such as GPIb and GPIIb/IIIa, are retained or partially retained on the surface of the freeze-dried platelets at the levels comparable to fresh platelets. The platelets and compositions of the invention also have characteristics that are not commonly found in fresh platelets, such as expression of charged lipids and granule proteins, such as P-selectin and Factor V. Due to this, the composition confers additional functions that fresh platelets can not perform, such as binding to Vitamin K-dependent proteins and the like. Further, the freeze-dried platelets can aggregate in response to collagen, arachidonic acid, and ristocetin, a characteristic that other freeze-dried platelets do not effectively have.

The compositions of the invention can comprise platelets from any source. That is, the compositions can comprise platelets from any mammalian species, including, but not limited to, humans, primates, canines, felines, bovines, ovines, porcines, equines, and rodents. They therefore can be platelets from a human, chimp, dog, cat, cow, sheep, pig, horse, mouse, or rat. In addition, the platelets can be autologous or heterologous, with respect to the blood that is being assayed, although in embodiments, the platelets used for calibration of an instrument are obtained from the same individual as the test samples (i.e., autologous platelets). In certain embodiments, the freeze-dried platelets originate from a pool of platelets obtained from two or more donors, who are heterologous as compared to the donor of the platelets for assay.

Platelets for use in the invention can be obtained from indated or outdated blood. Indated blood is blood that has freshly been obtained from a donor, and includes blood that is less than six days old. In contrast, outdated blood is blood that was obtained from a donor six or more days earlier, and thus is no longer deemed by governmental regulatory agencies as suitable for use as a therapeutic agent to treat excessive bleeding (e.g., for blood transfusions). In certain embodiments, outdated blood from one or multiple donor sources (used singly or as a mixture of blood from different sources) is used as a source of freeze-dried platelets to be used as a "normal" or "standard" control.

The freeze-dried platelets are present in the compositions in an amount of from $1 \times 10^5$ to $1 \times 10^{11}$. In embodiments where fresh platelets are present in the compositions, the fresh platelets are present in an amount of from $1 \times 10^5$ to $1 \times 10^{11}$. In exemplary embodiments, one or both type of platelets are present in a composition in amounts of about $1 \times 10^8$ to $1 \times 10^{10}$, such as about $1 \times 10^9$ to $9 \times 10^9$. When in a liquid composition, the platelets are present at concentrations ranging from $1 \times 10^5$ per milliliter (ml) to $1 \times 10^{11}$ per ml. In exemplary embodiments, the platelets are present in amounts of about $1 \times 10^8$ per ml to $1 \times 10^{10}$ per ml, such as about $1 \times 10^9$ per ml.

The pH of the composition may be any pH that is suitable for stability and function of platelets. Accordingly, it can range from mildly acidic to mildly basic, such as from pH 4.0 to pH 8.5. In various embodiments, the pH of the composition is 4.0, 4.5, 5.0, 5.5, 6.0, 6.5, 7.0, 7.5, 8.0, or 8.5. In other embodiments, the pH is any other pH within the range of 4.0 to 8.5. In embodiments where the platelets are in a solid (dry) state, the compositions may comprise one or more substance that, when hydrated, causes the pH of the resulting liquid composition to be in a suitable range.

The composition may further comprise a cryoprotectant, such as one containing DMSO or a polysaccharide. One non-limiting example of such a cryoprotectant is polysucrose Ficoll PM400. The cryoprotectant serves, in one function, to protect cells and platelets from lysis during the freezing process. It also may serve, in some situations, to protect cells and platelets from lysis during the thawing process. The cryoprotectant is not particularly limited in chemical nature, and can thus be selected from any of the numerous cryoprotectants known in the art.

In embodiments, the composition of the invention comprises DMSO, another aprotic solvent, or a combination of two or more aprotic solvents. The aprotic solvent may be included for any number of reasons, including as a cryoprotectant and as a cell membrane permeabilizer. While not being limited to any particular mode of action, it is believed that an aprotic solvent, such as DMSO, may act in the present compositions and methods to make platelet membranes more permeable to substances that improve the ability of platelets to withstand the freeze-drying process. For example, it is believed that one or more aprotic solvents can improve uptake of trehalose or another sugar prior to freeze-drying. While there are no particular limits to the amounts of aprotic solvent(s) present in the compositions, in general, the aprotic solvent is included at a ratio of about 2% (vol:vol) of a liquid composition. Where two or more solvents are included in the same composition, the total cumulative solvent amount of all aprotic solvents is used to determine the ratio. In general, the amount of aprotic solvent present depends on the number of platelets present in the composition. Typically, for production of lyophilized platelets, a liquid composition will comprise about $2 \times 10^9$ platelets in a 1 ml volume at the point where an aprotic solvent may be used. Under such circumstances, a 2% (vol:vol) final concentration of an aprotic solvent will be suitable. Broadly speaking, a concentration of aprotic solvent to total volume of a liquid composition can range from 0.1% to 10%, particularly where the aprotic solvent is non-toxic, such as DMSO.

The composition of the present invention may also or alternatively comprise cryoprecipitate or components of it, such as cryoprecipitate proteins. For example, the composition may comprise fibrinogen, Factor V, von Willerbrand Factor, or another plasma-derived protein. Many cryoprecipitate proteins are known in the art, and any one or more of them may be included in the composition. Likewise, portions of one or more may be included.

In embodiments where the platelets are in a solid (dry) state, the platelets or composition can be heated, such as at room temperature, 50° C., 55° C., 60° C., 65° C., 70° C., 75° C., 80° C., 85° C., or 90° C. In embodiments, the temperature is any temperature within the range of room temperature to about 90° C., or a temperature indicated below. The heating process can promote formation of platelets that are suitable for assays of platelet function.

In embodiments where the platelets are in a solid (dry) state, the composition can be heated from less than one minute up to 36 hours or more. Accordingly, the time of heating can be 0, 2, 4, 8, 12, or 24 hours. In other embodiments, the time of heating is any time within the range of less than 1 minute to 24 hours, including any minute or fraction thereof within that range.

As should be evident from the present disclosure, with the exception of certain drugs and anti-platelet compounds, any and all substances that are present in the compositions of the invention are preferably present in amounts that are compatible with at least one function of normal platelets. That is, the compositions of the invention may comprise numerous substances in addition to platelets, but each substance, and the total combination of substances, present is preferably present in an amount that permits the platelets to function normally, at least with respect to one platelet function. In embodiments where one or more substance is present in an amount that inhibits normal platelet function, it is preferred that the substance be removed or adjusted in concentration prior to use of the platelets in a method of the invention in order to permit the method to function well. Of course, these considerations are not relevant to drugs and other anti-platelet substances that are intentionally included in the compositions to determine the effect of such substances on platelet or clotting system function.

In another aspect, the invention provides a method of making freeze-dried platelets and compositions comprising freeze-dried platelets. In general, the method of this aspect of the invention comprises exposing platelets to at least one aprotic solvent, such as DMSO; exposing platelets to cryoprecipitate or a fraction of it, such as one containing fibrinogen and/or one or more other plasma proteins; and lyophilizing or freeze-drying the platelets. In embodiments, the method further comprises baking the freeze-dried platelets in a sealed container. The method may also comprise providing platelets for freeze-drying. A non-limiting example of a method of the invention is provided in the Examples, below.

According to the method of the invention, platelets are exposed to certain substances. As used herein, the step of exposing comprises any action that results in contact of a platelet with a substance that is provided and intended for contact with the platelet. Thus, exposing may comprise combining platelet(s) and substance(s) in an environment, and allowing the two to remain in the environment for an amount of time that is sufficient for the two to come into physical contact. Contact thus may occur through natural processes, such as diffusion through a liquid medium. Contact may also be accomplished, at least in part, through actions of a human or machine. For example, platelet(s) and substance(s) may be combined in the same environment (e.g., reaction tube) and the environment agitated or otherwise perturbed to cause the platelet(s) and substance(s) to move about in the environment. Non-limiting examples of such perturbations include mixing, stirring, vortexing, inverting, swirling, pipetting, and rocking.

Lyophilization may be accomplished through any technique that is suitable for freeze-drying of eukaryotic cells. Many different protocols and instruments for freeze-drying are known in the art, and any of these, and any combination of these, may be used. Freeze-drying techniques for platelets are known in the art, and any particular protocol may be used. In general, freeze drying comprises exposing the platelets to temperatures below 0° C. while applying a vacuum, and allowing the process of sublimation to remove all or essentially all of the water originally present in the platelets and their surroundings. The resulting platelets are in a solid (dry) form, and can be used in the methods of the invention, directly or after rehydration.

In embodiments, the method comprises providing platelets for treatment and lyophilization. In accordance with the discussion above, the platelets can be obtained from any suitable source. They can be, for example, human platelets, monkey platelets, dog platelets, cat platelets, horse platelets, cow platelets, sheep platelets, goat platelets, pig platelets, rabbit platelets, mouse platelets, or rat platelets. The platelets can be indated or outdated, and can be autologous or heterologous (with regard to the platelets with which they are to be assayed in a method of the invention, discussed below). Accordingly, they can be from random donors units or apheresis units. The amount of platelets can be any suitable amount, such as those described above.

The step of obtaining can comprise any activity that results in removal of platelets from a donor's body and transfer of the platelets into a receiving vessel. Numerous techniques for achieving this result are known in the art, and any method or combination of methods is encompassed by the present invention. In certain embodiments, obtaining comprises drawing blood from a donor's vein and placing the drawn blood in a tube, such as one made of plastic or glass.

In embodiments, the platelets are obtained from one or more blood donors, and are present in whole blood. It is preferable, however, that the platelets be purified, at least to some extent, from one or more other blood components. This is particularly so for freeze-dried platelets. Methods of purifying or isolating platelets from other blood components are well known to those of skill in the art, and thus need not be detailed here. In exemplary embodiments, platelets are purified from other blood components through a process that comprises centrifugation.

In practicing the method, one may separate platelets from other blood components by centrifuging. For example, one may pool all acceptable units of platelet rich plasma; adjust the pH to 6.2 to 6.8, preferably 6.4 to 6.8, more preferably 6.6 to 6.8, if necessary, for example by adding an acid or acidic solution; centrifuge the plasma at 750-2000×g, preferably 1000-1600×g, such as 1470×g for 5-30 minutes, preferably 10-20 minutes, such as 14 minutes; and remove platelet poor plasma from the platelet pellet, for example, by aspiration. During this process, one may optionally count the cells in the undiluted platelet rich plasma using an $A^C$.T Coulter Counter or equivalent instrument.

If the original platelet source was a random donor unit, one may perform the following red blood cell removal steps. Divide the platelet rich plasma equally and centrifuge the plasma in a swinging bucket centrifuge for 3-15 minutes, preferably 3-5 minutes, at 500-1000×g, preferably 650-850× g, such as 750×g, at room temperature. Remove the platelet rich plasma and pool it in a clean container, such as a plastic beaker, leaving behind the pellet of red blood cells at the bottom of the conical tubes. One may then take the platelet cell count of the platelet rich plasma and dilute if necessary to be within the linear range of the instrument for platelet count.

According to the method, platelets are exposed to an aprotic solvent, such as DMSO. In embodiments, the platelets are suspended gently in phosphate buffered saline-EDTA (PBSE), pH 7.4, and DMSO is added at a rate of 1-50 microliters (ul), preferably 10-20 ul, such as 10 ul per $1 \times 10^9$ platelets. The platelet-DMSO mixture may be incubated at room temperature (21-25° C.) for less than 1 minute up to 2 hours or more, preferably from 15 minutes to 45 minutes, such as for 30 minutes. During this time, the mixture may be gently shaken or mixed, such as by way of an orbital shaker at about 35-65 rpm, such as 50 rpm.

The method may further comprise isolating the treated platelets, such as by centrifugation. For example, the platelet-DMSO mixture may be diluted by addition of a sufficient amount of PBSE, pH 6.5, to lower the pH of the mixture to about pH 6.5-6.7. For example, approximately twice the volume of the platelet-DMSO mixture may be added to achieve the desired pH range. The diluted, pH adjusted platelet mixture can then be centrifuged to separate the platelets from other substances in the mixture. For example, the mixture may be centrifuged in a swinging bucket rotor at 500-2000×g, preferably 750-1500×g, such as 1000×g, for 5-30 minutes, preferably 6-15 minutes, such as 10 minutes. The supernatant may then be removed to isolate the platelets in the pellet.

The method of the invention comprises re-suspending isolated platelets in a liquid, which is referred to herein as a resuspension liquid or a loading buffer. The resuspension liquid comprises at least one buffering agent (also referred to herein as a buffer) that does not interfere with platelet function in vitro or in vivo, such as HEPES buffer or sodium bicarbonate ($NaHCO_3$). The buffer can be at any suitable concentration that provides buffering capacity at the temperature ranges of interest. Fore example, the buffer may be HEPES buffer at a range of from 5-15 mM, such as from 9-10 mM, for example, 9.5 mM. The buffer may also or alternatively be $NaHCO_3$, which may be present at a range of from 5-15 mM, such as from 8-12 mM or 10-14 mM, for example at about 12 mM.

The resuspension liquid also comprises one or more biologically compatible salts, such as NaCl and KCl. The salts are included to provide a proper isotonic composition, and any suitable combination of salts may be used. For example, NaCl may be added in an amount of from 50-100 mM, such as from 70-80 mM, for example, at 75 mM. Likewise, KCl may be added in an amount of from 1-10 mM, such as from 3-7 mM or 4-6 mM, for example from 4.5-5.1 mM or about 4.8 mM.

The resuspension liquid also comprises at least one sugar, such as glucose and trehalose, each sugar having the same or a different function within the composition. The sugars can be included independently in the liquid composition in an amount ranging from 1-250 mM, such as from 1-150 mM, from 1-110 mM, from 1-100 mM, from 1-50 mM, from 1-25 mM, and from 1-10 mM. For example, the liquid composition may comprise one or more sugars, independently at a concentration of 1 mM, 2 mM, 3 mM, 4 mM, 5 mM, 6 mM, 7 mM, 8 mM, 9 mM, 10 mM, 20 mM, 40 mM, 75 mM, or any other specific value within the ranges disclosed herein.

The resuspension liquid further comprises at least one alcohol, such as ethanol (EtOH), which can be present in an amount of 0.1-10%, such as from 0.5-5%, 0.75-1.5%, for example at 1%.

It is to be understood that all ranges disclosed herein are intended as a specific disclosure of each value within the range, such specific values being immediately apparent to those of skill in the art without the need for listing of each value. Thus, for example, a disclosure of a range of 1-100 will include a disclosure of the value 90 without the need to specifically enumerate that value.

As a general matter, the resuspension liquid is suitable for use in loading sugars, such as trehalose, into platelets. Without being limited to any particular mode of action, it is believed that the salts maintain the isotonicity of the composition, while sugars and alcohols aid in the uptake by platelets of a sugar to be loaded, such as trehalose.

Furthermore, as a general rule, the platelets are re-suspended in a minimal volume of the loading buffer solution (i.e., in a volume that is just adequate to resuspend the platelets, such as an equivalent volume of the platelets). Thus, the term minimum volume will vary depending on the size or amount of platelets to be treated. It thus may range from 100-500 microliters for a production batch, or be greater or lesser.

The re-suspended platelets are maintained in the buffer for a period of time at an elevated temperature. For example, the platelets can be incubated at a temperature between 22° C. and 40° C., preferably between 30° C. and 40° C., such as at 37° C. The incubation can be performed for any amount of time required for the solution to achieve a temperature of greater than 30° C., preferably at or about 37° C. For example, the incubation can be performed for 1-4 hours or any fraction of an hour (e.g., minutes, seconds) within this range. In embodiments, the incubation occurs from 1.5-2.5 hours, such as 2 hours. In exemplary embodiments, the incubation is performed at 37° C. for 2 hours. Any suitable instrument for raising the temperature may be used, including an incubator and a water bath. During the incubation, the solution may be mixed or otherwise agitated to aid in suspension of the platelets, exposure of the platelets to the buffer components, and distribution of heat within the solution.

According to the method of the invention, platelets are contacted with a polysaccharide. This contacting act is also referred to herein as "loading" of the platelets. Loading may be accomplished by any suitable technique, but is preferably accomplished, at least in part, by adding at least one polysaccharide to the platelet/loading buffer composition. In embodiments, the polysaccharide comprises polysucrose, as in the form of polysucrose Ficoll PM400. In general, adequate polysaccharide is added to the composition to achieve a final polysaccharide concentration range (w/v) of from 2%-10%, preferably from 4%-8%, such as 6%. Thus, a concentrated solution of polysaccharide may be added to the platelet mixture. For example, 1/10 volume of a 60% polysaccharide solution may be added; 1/5 volume of a 30% polysaccharide solution may be added, 1/10 of a 40% polysaccharide solution may be added, etc.

The method of making freeze-dried platelets comprises contacting platelets with cryoprecipitate or a fraction thereof, such as a fraction comprising fibrinogen or another plasma protein. In embodiments, the cryoprecipitate is added to the platelet-containing mixture to achieve a fibrinogen concentration of between 0.25 milligram per milliliter (mg/ml) to 5 mg/ml, such as 0.75 mg/ml up to 3 mg/ml. For example, one may add sufficient cryoprecipitate to achieve a final fibrinogen concentration of less than 0.5 mg/ml up to 4 mg/ml or more. Thus, the final concentration may be about or exactly 0.5 mg/ml, 1 mg/ml, 1.5 mg/ml, 2.0 mg/ml, 2.5 mg/ml, or 3.0 mg/ml. Alternatively or additionally, Factor VIII may be used as a benchmark for the amount of cryoprecipitate to be added. In these cases, the cryoprecipitate is added to the platelet-containing mixture to achieve a Factor VIII concentration of between 0.1 unit per milliliter (U/ml) and 3 U/ml, such as between 0.3 U/ml and 1 U/ml. Alternatively or additionally, Factor XIII may be used as a benchmark for addition of cryoprecipitate. Where used as a benchmark, an amount of cryoprecipitate should be added to achieve a concentration of Factor XIII of from 0.1 U/ml to 2 U/ml, such as between 0.15 U/ml and 0.6 U/ml. Of course, any particular amounts within these specified ranges may be achieved, and one of skill in the art would immediately recognize each particular amount without the need to specifically recite each amount herein.

The method comprises lyophilizing the loaded platelets. Numerous techniques for lyophilization of cells are known and any such technique that is suitable for lyophilization of eukaryotic cells may be used according to the present invention.

After lyophilization, the platelets and/or composition comprising platelets may be heated to improve stability and function of the platelets upon re-hydration. Heating may be effected through any technique that is suitable, including but not limited to baking in an oven or incubator. Heating may be accomplished at any suitable temperature within the range of 40° C. to 100° C., preferably between 50° C. and 80° C., such as at 80° C. In embodiments, the platelets and/or composition can be heated from less than six minutes up to 48 hours or more, such as between 12 and 36 hours. Accordingly, the time of heating can be 1, 2, 4, 6, 8, 10, 12, 24, or 36 hours. As with the ranges presented above, one of skill in the art will immediately recognize that any and all specific temperatures and times within the ranges given above are envisioned by the present invention, and are immediately apparent to the skilled practitioner. Accordingly, each of the various specific temperatures and times within the disclosed ranges need not be recited specifically herein.

In embodiments, the method comprises sterilizing the lyophilized material using any known technique that is suitable for sterilizing lyophilized materials, including, but not limited to, irradiation. In situations where the time and temperature for heating is adequate, the heating step may also be a sterilization step.

In certain embodiments, the method of making the platelets and/or compositions comprises providing blood or a blood product that contains platelets; optionally removing all or essentially all red and white blood cells that might be present in the blood or blood product; adjusting the pH of the resulting cell-free material to an acidic pH, such as pH 6.7; separating platelets from all or essentially all other components present in the material; re-suspending the platelets in a liquid comprising an aprotic solvent; isolating the platelets; loading the platelets with a polysaccharide, such as polysucrose Ficoll PM400; loading the platelets with cryoprecipitate or a fraction thereof, and lyophilizing. Optionally, the lyophilized platelets may be baked in a sealed container, such as at 80° C. for 24 hours.

While the compositions of the invention may be dry compositions, in embodiments, the compositions comprise water and/or another biologically tolerable solvent. Accordingly, in embodiments of making the freeze dried platelets and compositions, the method comprises reconstituting or re-hydrating the freeze-dried platelets with a liquid. Re-hydrating can comprise adding water or an aqueous solution to the freeze-dried platelets in an amount sufficient to restore at least one physical or biological property to the platelets. Re-hydrating can be through any suitable method known in the art, including, but not limited to, direct addition of liquid water or another liquid composition to the platelets, and slow vapor reconstitution. Aqueous solutions may comprise any substances that are compatible with platelet function in the amounts in which they are present in the compositions.

The methods of making a composition of the invention can further comprise combining the freeze-dried platelets with other platelets, to form a mixture. The other platelets may be freeze-dried platelets, or may be platelets that are present in a liquid composition, such as blood or a blood fraction (e.g., blood plasma). The mixture is typically, but not always, made in a reaction vessel in which clotting can be detected. That is, although it is possible to make the mixture in vivo by injecting the freeze-dried platelets into a body, typically, the freeze-dried platelets are combined with the other platelets outside of a body, such as in a reaction vessel suitable for detection of blood clots.

The method of making a composition may further comprise adding one or more substances that have biological activity. For example, the method may comprise adding to a composition comprising the freeze-dried platelets one or more drug or other substance, which may have anti-platelet activity. Exemplary drugs and substances with anti-platelet activities are discussed above.

Furthermore the method of making a composition may further comprise adding one or more biological molecules that have enzymatic activity. For example, the method may comprise adding to a composition comprising the freeze-dried platelets one or more coagulation proteins or other substance, which may attenuate platelet activity. Exemplary drugs and substances which attenuate platelet activities are discussed above.

Likewise, the method may further comprise adding one or more fluorescence molecules to the freeze-dried platelets. For example, the method may comprise adding to a composition comprising the freeze-dried platelets one or more fluorescein or other fluorescence substances, which may enhance the signaling of platelet activity. Fluorescence substances that may be added include, but are not limited to, BODIPY (dipyrromethenboran difluoride), acridine orange, rhodamine, green fluorescent protein (GFP), R-phycoerythrin, and cyanine dyes.

As a result of the methods disclosed herein, the freeze-dried platelets and compositions comprising them can be stored for extended periods of time prior to use, and retain essentially of all of their blood clotting functions during storage and through reconstitution. The methods of making the freeze-dried platelets and compositions are thus, in embodiments, methods of making stabilized freeze-dried platelets.

As discussed below, the freeze-dried platelets and compositions according to the present invention are useful for diagnosing various diseases and disorders of the blood clotting system, and as control reagents for clotting reactions. They are particularly useful in in vitro settings, such as diagnostic reactions.

In yet another aspect, the present invention provides a method of diagnosing a disease or disorder of the blood clotting system. In general, the method comprises: combining freeze-dried platelets of the invention with platelets and/or plasma removed from a patient having, or suspected of having, a disease or disorder of the blood clotting system to form a mixture, and determining whether the person has a defect in the blood clotting system by assaying one or more biological or biochemical functions of the mixture, where the defect decreases or abolishes the patient's blood clotting system's ability to function normally or to cause clot formation in a pre-defined period of time. Typically, determining whether the patient's blood clotting system is defective comprises assaying clotting time of the mixture According to the invention, the disease or disorder may be any disease or disorder that affects the ability of blood to clot. The disease thus may involve a defect in Glycoprotein IIb/IIIa, Glycoprotein Ib, von Willebrand Factor, and fibrinogen. The disease or disorder thus may be, among other things, afibrinogenemia, thromlasthenia, vWF disease, Bernard Souleir Syndrome, one or more of the Receptor Defects Disorders of secretion/signal transduction, Storage Pool Deficiency, Diminished Thromboxane Synthesis, one or more of the Signal Transduction/Primary Secretion Defects, or a Deficiency of Platelet Coagulant Activities.

In embodiments, the method comprises combining freeze-dried platelets of the invention with fresh platelets or plasma, and determining whether the mixture has normal levels of one or more function of the blood clotting system, an abnormal level (be it high or low) indicating a disease or disorder.

The freeze-dried platelets may be obtained from one or more donors with a known status with respect to the clotting system (e.g., having a fully functional clotting system, or having a defect in one or more clotting factors). When the freeze-dried platelets are obtained from mixtures of platelets from a public blood bank, they can be assumed to be "normal" or "fully functional" with regard to platelet function. Alternatively, the freeze-dried platelets may be obtained from a patient undergoing or about to undergo a treatment regimen that might affect platelet function. Likewise, the freeze-dried platelets can be obtained from a patient who has completed a treatment regimen that has, or might have, affected platelet function (whether the patient had completed the full treatment regimen or was removed from the regimen early due to adverse side-effects).

Like the freeze-dried platelets, the fresh platelets or plasma may be obtained from one or more donors with a known status with respect to the clotting system (e.g., having a fully functional clotting system, or having a defect in one or more clotting factors). When the fresh platelets or plasma are obtained from mixtures from a public blood bank, they can be assumed to be "normal" or "fully functional" with regard to platelet function or plasma complement. Alternatively, the fresh platelets or plasma may be obtained from a patient undergoing or about to undergo a treatment regimen that might affect platelet function. Likewise, the fresh platelets or plasma can be obtained from a patient who has completed a treatment regimen that has, or might have, affected platelet function (whether the patient had completed the full treatment regimen or was removed from the regimen early due to adverse side-effects).

Regardless of the source of the freeze-dried platelets and the fresh platelets or plasma, the method comprises combining the two to make a mixture. The mixture is then assayed for one or more biological or biochemical functions of the mixture. Preferably, one or more functions of the clotting system, such as the ability to aggregate, are assayed. Comparison of the level of function or activity of the chosen functions or activities to "normal" levels permits one to determine if there is a difference in the levels. A difference in the levels indicates the presence of a disease or disorder of the blood clotting system.

In exemplary embodiments, the method comprises combining freeze-dried platelets that were obtained from a public blood bank with fresh platelets that were removed from a patient having, or suspected of having, a disease or disorder of the blood clotting system to form a mixture, and determining whether the person has a defect in the blood clotting system by assaying one or more biological or biochemical functions of the mixture. According to this aspect of the invention, the defect, if present, decreases or abolishes the patient's blood clotting system's ability to function normally or to cause clot formation in a pre-defined period of time.

In other exemplary embodiments, the method comprises combining freeze-dried platelets obtained from a patient prior to initiation of a treatment regimen with fresh platelets or plasma obtained from the patient at one or more times during or after completion of the treatment regimen to form a mixture. The method further comprises determining the clotting ability of the mixture(s), the ability indicating whether the treatment regimen induced a disease or disorder of the clotting system, or exacerbated an underlying, but never recognized, disease or disorder of the clotting system of the patient.

The freeze-dried platelets and platelets from the patient may be provided from any source, in accordance with the discussion above. Combining of the two can be by any suitable method, such as those well known in the art for combining two eukaryotic cells. Furthermore, determining whether the patient has one or more defect in the blood clotting system can be accomplished by any suitable technique, as discussed above.

In embodiments, determining comprises detecting the presence or amount of aggregation of platelets in the mixture. In general, low levels of aggregation indicate a defect or deficiency in blood clotting activity, whereas high levels of aggregation indicate normal or acceptable levels of activity. Typically, determining whether the patient's blood clotting system is defective comprises assaying clotting time of the mixture.

The method can comprise other steps in addition to the basic steps disclosed above. For example, the method can comprise obtaining freeze-dried platelets prior to combining them with blood. In embodiments, the freeze-dried platelets are obtained from the patient for whom the assay is being performed, and are platelets that were obtained at an earlier time, such as prior to initiation of a drug regimen. The method can also comprise adding one or more drugs or other substances, which have a known effect on platelets or other participating cells or molecules of the clotting system, to the platelets, and determining the effect of the addition on clotting function. By selecting specific drugs with known activities, it is possible to determine the precise cause of the disease or disorder. With such knowledge, appropriate treatment regimens may be implemented.

In an additional aspect, the invention provides a method of monitoring the progression of a disease or disorder of the blood clotting system. In general, the method comprises: combining freeze-dried platelets of the invention with platelets and/or plasma removed from the patient suffering from the disease or disorder to make a mixture, and determining the blood clotting ability of the mixture. Typically, determining the blood clotting ability of the mixture indicates the blood clotting ability of the patient's blood. In addition, typically the act of determining comprises assaying clotting time of the mixture. Furthermore, typically, multiple assays are performed over time to give an indication of any progression of the disease or disorder over that time. By comparison of two time points, one can determine if a change in the status of the disease or disorder (if present) has occurred between the two time points. This information can, among other things, aid a doctor or patient in deciding whether to continue a particular treatment regimen. Furthermore, typically, multiple assays are performed over time to give an indication of progression of the disease or disorder over time.

As with other methods of the invention, various drugs or other substances can be added to the assay mixture to determine the specific defect in the disease or disorder. Knowledge of the specific source of the defect may enable treatment regimens to be developed. Non-limiting examples of the various drugs or other substances are mentioned above.

In another aspect, the invention provides a method of monitoring the effects of a treatment regimen for a patient on the blood clotting system of that patient. In general, the method comprises: combining freeze-dried platelets of the invention with platelets and/or plasma removed from the patient undergoing the treatment regimen to make a mixture, and determining the blood clotting ability of the mixture. Preferably, the method is repeated at least one time during the treatment regimen, and the results compared. In some embodiments, the method comprises performing the method steps on platelets and/or plasma removed from the patient prior to commencement of the treatment regimen. Typically, determining the blood clotting ability of the mixture indicates the blood clotting ability of the patient's blood, and comprises assaying clotting time of the mixture. Furthermore, typically, multiple assays are performed over time to give an indication of the effects of the treatment regimen over time. By comparison of two or more time points, one can monitor the effects of a treatment regimen on the blood clotting system of that person.

As with the method of diagnosis, in practicing the method of monitoring, one may obtain platelets for preparation of the freeze-dried platelets from a public source or from a patient prior to initiation of a treatment regimen. One may also obtain fresh platelets or plasma from a patient or a public source prior to initiation of a treatment regimen. Likewise, one may obtain fresh platelets or plasma from the patient one or more times during the treatment regimen.

The method of monitoring comprises determining the blood clotting ability of combinations of freeze-dried and fresh components. Typically, determining the blood clotting ability of the mixture indicates the blood clotting ability of the patient's blood, and comprises assaying clotting time of the mixture. Furthermore, typically, multiple assays are performed over time to give an indication of the effects of the treatment regimen over time.

Numerous treatments for a variety of diseases and disorders are available to the public. Some of these treatments, while effectively treating a particular disease or disorder, result in unintended effects (i.e., side-effects) that diminish or abolish one or more functions of the blood clotting system. Other treatments are specifically designed to promote or inhibit the activity of a patient's blood clotting system. In any event, it is often desirable to monitor the presence and/or concentration of drugs in the blood of a patient, and in particular monitor the effect of those drugs on the patient's blood clotting activity. The present methods permit one to monitor such effects simply and rapidly.

It is to be noted that all of the methods of monitoring and diagnosing can comprise one or more control reactions. The concept of control reactions is well known to those of skill in the art, and numerous types of control reactions can be included in the methods of the present invention to monitor the effectiveness and success of one or more steps in the methods. Among the more common control reactions that can be performed are reactions that involve freeze-dried platelets as the sole source of platelets, reactions that involve fresh platelets as the sole source of platelets, reactions in which one or more known substances (with known effects on platelet function or clotting system function) are exposed to fresh platelets (e.g., a positive control), and reactions in which no substance in addition to platelets is added (e.g., a negative control). Included among the control reactions are reactions that generate a standard curve. Because the methods of the present invention provide repeatable aggregation characteristics when performed with accurately measured amounts of normal freeze-dried platelets and normal serum or blood, standard curves can be generated, and these standard curves can be used as a basis for comparison of test samples for any number of characteristics, including, but not limited to, platelet number/concentration, ability of the platelets to participate in clotting, and presence or absence of functional surface proteins on platelets.

It is also to be noted that, although the methods were disclosed as being suitable for use with freeze-dried platelets and fresh platelets or plasma, freeze-dried platelets can be combined according to the methods of the invention with whole blood, platelets, plasma, purified coagulation proteins, and other components of the blood system. Use of the terms "fresh platelets" and/or "fresh plasma" is to be understood to encompass all other types of fresh blood products. Furthermore, the term "fresh" does not necessarily require a strict time-dependency. Rather, it is used solely to differentiate between freeze-dried platelets and non-freeze-dried substances.

The methods of the invention may also comprise performing the method more than one time on the same sample, under the same conditions. As is known in the art, performing a method on multiple identical samples provides an indication of the reliability and reproducibility of the method. According to the present invention, each step in a method, or only certain steps within the method, can be repeated according to this embodiment of the invention.

As is evident from the above description, all the methods of detection and monitoring can encompass the general concept of determining platelet counts or function levels by assaying clot time. Thus, the methods of the invention can be considered, in embodiments, as methods of determining platelet counts of a sample comprising platelets. Likewise, the methods of the invention can be considered, in embodiments, as methods of determining platelet function of a sample comprising platelets. Typically, platelet function is assayed by the ability to participate in the clotting process.

The freeze-dried platelets of the invention show many characteristics of fresh platelets. Among those characteristics is size and clotting ability. The freeze-dried platelets of the invention are of about the same size as fresh platelets and show a similar ability as fresh platelets to clot under appropriate conditions. Thus, the freeze-dried platelets can be used to calibrate instruments for detection and study of platelets. Being freeze-dried, the platelets of the invention are advantageously used for calibrating machinery because calibration can be accomplished at any convenient time, rather than in a small window of opportunity provided by fresh platelets. Thus, the freeze-dried platelets of the invention, and reconstituted platelets derived therefrom, find use as control reagents for instruments and protocols that measure one or more function of platelets. They thus can be, among other things, calibrating reagents for platelet poor plasma, diagnostic reagents for coagulation factor defects, diagnostic tools to identify specific coagulation factor defects, and control reagents to monitor Vitamin-K dependent clotting factors.

Given the fact that the freeze-dried platelets of the invention have the same size and biochemical makeup as fresh platelets, the freeze-dried platelets, upon reconstitution, can be used as a calibrating reagent to ensure that the machine can detect and extrapolate true platelet functions. The freeze-dried platelets can be used as a calibration reagent to evaluate performance parameters of instruments before samples containing fresh platelets are used. Furthermore, because freeze-dried platelets of the invention have many, if not all, of the biochemical characteristics of fresh platelets, it is possible that the freeze-dried platelets will respond to the same stimuli as fresh platelets and produce the same biochemical responses as fresh platelets. For example, if one wants to test for the activity of a hemostatic reagent, such as Factor IXa, one can look at the enzymatic activities of Factor IXa in the presence and absence of freeze-dried platelets. The result from such an experiment will allow correlation between Factor IXa and fresh platelets.

In an additional aspect, the invention provides kits for performing the methods of the invention. Typically, the kits of the invention comprise freeze-dried platelets. The kits can also comprise some or all of the other reagents and supplies necessary to perform at least one embodiment of one method of the invention. For example, the kits can comprise one or more drugs that affect the ability of platelets to participate in the clotting system. Thus, the kits can be diagnostic kits, blood clotting monitoring kits, or drug treatment monitoring kits. Often, the kits will comprise some or all of the supplies and reagents to perform one or more control reactions to ensure the kits are performing properly and to provide baseline results against which test samples can be compared.

In its simplest form, a kit according to the invention comprises a container containing platelets or at least one composition according to the invention. Thus, in embodiments, the kit of the invention comprises a container containing freeze-dried platelets or a composition comprising freeze-dried platelets. In other embodiments, the kit comprises multiple containers, each of which may contain freeze-dried platelets, compositions comprising freeze-dried platelets, or other substances that are useful for performing one or more embodiments of a method of the invention. In other embodiments, the kit comprises additional components, which may be contained in the same or one or more different containers. In its various forms, the kit of the invention can comprise substances that are useful for detection and/or study of platelet function; for calibrating instruments; for calibrating platelet size; for calibrating differential gradient separation techniques; as research tools to examine the interaction of platelet receptors and their ligands; to study surface mediated enzymatic reactions, including but not limited to tenase complex, prothrombinase complex, and the like; to study platelet aggregation, whether mechanical or biochemically induced; to study platelet biology and storage; to isolate platelet-related surface molecules; to isolate and purify platelet cytoplasmic molecules or platelet granules (alpha and dense granules); to study platelet and microparticle interactions; to study anti-platelet medications; to study platelet inhibitors; to determine platelet inhibitors that can be tailored to individuals; to study neuropsychopharmacology; to study inflammation, coagulation, cellular repair, and regeneration; to study neo-antigenicity in platelet therapies; to characterize non-MHC antigens that promote immune responses against blood cells; to study the effect of blood-borne pathogens; to image normal and damaged blood vessels; and to study angiogenesis, atherosclerosis, thrombosis, and cardiovascular disease.

The container can be any material suitable for containing a composition of the invention or another substance useful in performing a method of the invention. Thus, the container may be a vial or ampule. It can be fabricated from any suitable material, such as glass, plastic, metal, or paper or a paper product. In embodiments, it is a glass or plastic ampule or vial that can be sealed, such as by a stopper, a stopper and crimp seal, or a plastic or metal cap. In general, the container and seal are made of materials that can be sterilized by heat (dry or wet), radiation (UV, gamma, etc.), or exposure to chemicals. Preferably, the container is sterilized before the composition of the invention is introduced into the container. Typically, the container will be of sufficient size to contain the composition of the invention, yet have head space to permit addition of additional substances, such as sterile water or saline or a mixture of the two, which can be used to re-hydrate the composition in the container. In embodiments, the container comprises a sufficient amount of platelet-containing material to perform at least one assay of one embodiment of the method according to the invention. The amount of platelet-containing material contained in the container can be selected by one of skill in the art without undue experimentation based on numerous parameters that are relevant to performing an assay according to the invention (including optional control reactions and repeating of the assay) and packaging and storing of the kit.

In embodiments, the container is provided as a component of a larger unit that typically comprises packaging materials (referred to below as a kit for simplicity purposes). The kit of the invention can include suitable packaging and, optionally, instructions and/or other information relating to use of the compositions. Typically, the kit is fabricated from a sturdy material, such as cardboard or plastic, and can contain the instructions or other information printed directly on it. In embodiments, the kit comprises other components, such as, but not limited to, purified components of the clotting cascade and drugs affecting the clotting cascade. The kit can comprise multiple containers containing the composition of the invention. In such kits, each container can be the same size, and contain the same amount of composition, as each other container, or different containers may be different sizes and/or contain different amounts of compositions or compositions having different constituents. One of skill in the art will immediately appreciate that numerous different configurations of container sizes and contents are envisioned by this invention, and thus not all permutations need be specifically recited herein.

In general, the kit comprises containers to contain the components of the kit, and is considered a single package comprising a combination of containers. Thus, the components are said to be in packaged combination within the kit. In addition to a container containing the composition of the invention, the kit can comprise additional containers containing additional compositions of the invention. Each container may contain enough platelets for a single performance of an embodiment of the method of the invention, or it may contain enough for two or more performances. The various containers may contain differing amounts of the composition of the invention. Thus, in embodiments, the kit comprises a sufficient amount of platelets to perform and embodiment of the method according to the invention. In embodiments, the kit comprises other components, such as purified components of the clotting cascade. The kit can further comprise some or all of the supplies and materials needed to prepare for and perform a method of the invention, such as, but not limited to, sterile water or a sterile aqueous solution (e.g., saline). In some embodiments, the kits comprise one or more liquids to hydrate the compositions of the kits. The liquid may be any suitable liquid, but is typically a water-based liquid, such as water or saline.

EXAMPLES

The invention will be further explained by the following Examples, which are intended to be purely exemplary of the invention, and should not be considered as limiting the invention in any way.

The Examples provided herein show the preparation of freeze-dried platelets according to an embodiment of the invention, and use of those platelets in clotting reactions.

Example 1

Initial Preparation of Reagents and Platelets

Buffers and Solutions:
Suspension Buffer:
9.5 mM HEPES
75 mM NaCl
4.8 mM KCl
5 mM glucose
12 mM $NAHCO_3$
100 mM Trehalose
1% EtOH
Stock Solutions and Reagents:
30% Polysucrose Solution (12 g Polysucrose Ficoll™ PM400 in 40 ml water)
1×PBS (standard solution)
PBSE, pH 7.4 (PBS plus 10 mM EDTA)
PBSE, pH 6.5

Remove all buffers and other reagents from refrigerators, freezers, and other storage areas. Allow each to reach ambient temperature (approximately 21° C.-25° C.). All buffers that require daily preparation should be made while previously prepared buffers are warming. When platelet units arrived, they should be placed on an orbital shaker reciprocating at approximately 50 RPM until use.

Example 2

Initial Preparation of Pooled Plasma

If using more than one unit of plasma, pool all acceptable units of platelet rich plasma (PRP) in one large plastic beaker. Take a platelet cell count of the undiluted pooled PRP on an instrument suitable for platelet counting, such as the $A^C$•T 10 Coulter counter. Stir and measure the pH of the PRP. If the pH is greater than 6.8, adjust the pH to between 6.4 and 6.8 with ACD. If the pH adjustment is overshot (too much ACD added) to between 6.2-6.4, verify that the platelets are still swirling and if so, continue to the next step.

If the original platelet source was an apheresis unit, skip the following step. If the original platelet source was a random donor unit (RDU), perform the following RBC removal step. Divide PRP equally between 50 ml conical tubes. Spin the PRP in a swinging bucket centrifuge for 3 to 5 minutes at 750×g at room temperature. Remove the PRP and pool in a clean plastic beaker, leaving behind the pellet of RBCs at the bottom of the conical tubes. Take platelet cell count of PRP (dilute if necessary to be within the linear range of the instrument for platelet count).

Aliquot PRP into clean 50 mL conical tubes.

Pellet platelets by spinning at 1470×g for 14 minutes at room temperature.

Aspirate platelet poor plasma (PPP) with a transfer pipette. Set aside the PPP.

Example 3

Preparation of Lyophilized Platelets

DMSO Incubation

Resuspend platelets gently in a small volume of PBSE, pH7.4, taking care not to mix vigorously, resulting in activation of platelets. Where possible, use gentle "puffs" of PBSE, pH 7.4 to resuspend the platelets.

Add 10 ul of DMSO for every $1×10^9$ platelets total.

Incubate platelets with DMSO at room temperature for 30 minutes while shaking gently on an orbital shaker (~50 RPM).

After incubation, gently add a large volume of PBSE, pH6.5 to the platelet samples with a transfer pipette until the samples reach a pH of 6.5-6.7.

Aliquot out the resuspended platelets evenly between clean conical centrifuge tubes.

Centrifuge the platelets in a swinging bucket centrifuge at 1000×g for 10 minutes at room temperature. After the spin, remove the supernatant, leaving the platelet pellet in the bottom of the conical tube.

Platelet Loading

Resuspend the platelet pellet in a minimal volume of Suspension Buffer by gentle mixing with a transfer pipette. Pool all resuspended platelets.

Incubate the platelets in a 37° C. water bath for 2 hours, gently inverting the platelets every 30 minutes, then remove the platelets from the water bath.

Add enough 30% polysucrose to the platelets with to have a final polysucrose concentration of 6%.

Add enough thawed cryoprecipitate to the platelets to have a final fibrinogen concentration of at least 1 mg/ml.

Lyophilization

Aliquot the final platelet mixture in 0.5 ml aliquots into glass serum vials.

Lyophilize platelets using any standard instrument, according to the manufacturer's instructions or protocols typically used to lyophilize eukaryotic cells.

After lyophilization, seal vials under a vacuum, and cap immediately with aluminum seals.

Bake the sealed vials in an incubator at 80° C. for 24 hours.

When ready for use, rehydration is by 0.5 ml of deionized ultrafiltered $H_2O$ added directly to the cake. Wait 5 minutes for full rehydration before use.

Example 4

Use of Freeze-Dried Platelets as Calibrating Agent

Freeze-dried platelets made according to the method indicated in Examples 1-3 were tested for suitability for use with an aggregometer, and in particular as a control reagent for aggregometers in conjunction with thrombin. More specifically, in a standard light transmission aggregometer, a solution of $200\text{-}400\times10^3$ freeze-dried platelets per microliter in cation-free HMTA Buffer was prepared, and to it 2.5 ul of 0.2 M $CaCl_2$ and 2.5 ul of 0.2 M $MgCl_2$ was added. To determine the response to thrombin, 2.5 ul of 1000 U/ml thrombin was added, and a trace was run for 15 minutes.

As can be seen from the graph of FIG. 1, when recalcified with 4 micromolar (uM) $CaCl_2$, the freeze-dried platelets respond well to collagen, arachidonic acid, and ristocetin. The platelets respond strongly to 10 ug/ml collagen, producing a smooth curve with a steep slope. Moreover, collagen elicits an average percent aggregation of 61.3% (n=6), and a functional range of 58-65%. Also, the platelets respond reliably to 500 ug/ml of arachidonic acid, producing a consistent curve with an average percent aggregation of 37.3% (n=4), and a range of 32-42%. Ristocetin proves slightly less reliable in the sense that the curve it produces is often erratic; however, ristocetin always yields an aggregation reaction, regardless of its appearance. The curve is often irregular, with a range of values for slope, and a rough line response. These facts aside, ristocetin (1500 ug/ml) produces an average percent aggregation of 26.7% (n=3), with a range of 20-35%. It was also found that the platelets do not respond to ADP or epinephrine. The graph of FIG. 1 shows a typical response to these three aforementioned agonists. The line corresponding to Channel 1 represents freeze-dried platelets without recalcification and without the addition of an agonist. The line corresponding to Channel 2 is a trace of the platelet's response to 10 ug/ml of collagen, while the line corresponding to Channel 3 is a trace of the platelet's response to 1500 ug/ml of ristocetin. The line corresponding to Channel 4 is a trace of the platelet's response to 500 ug/ml of arachidonic acid.

Example 5

Figure 2:
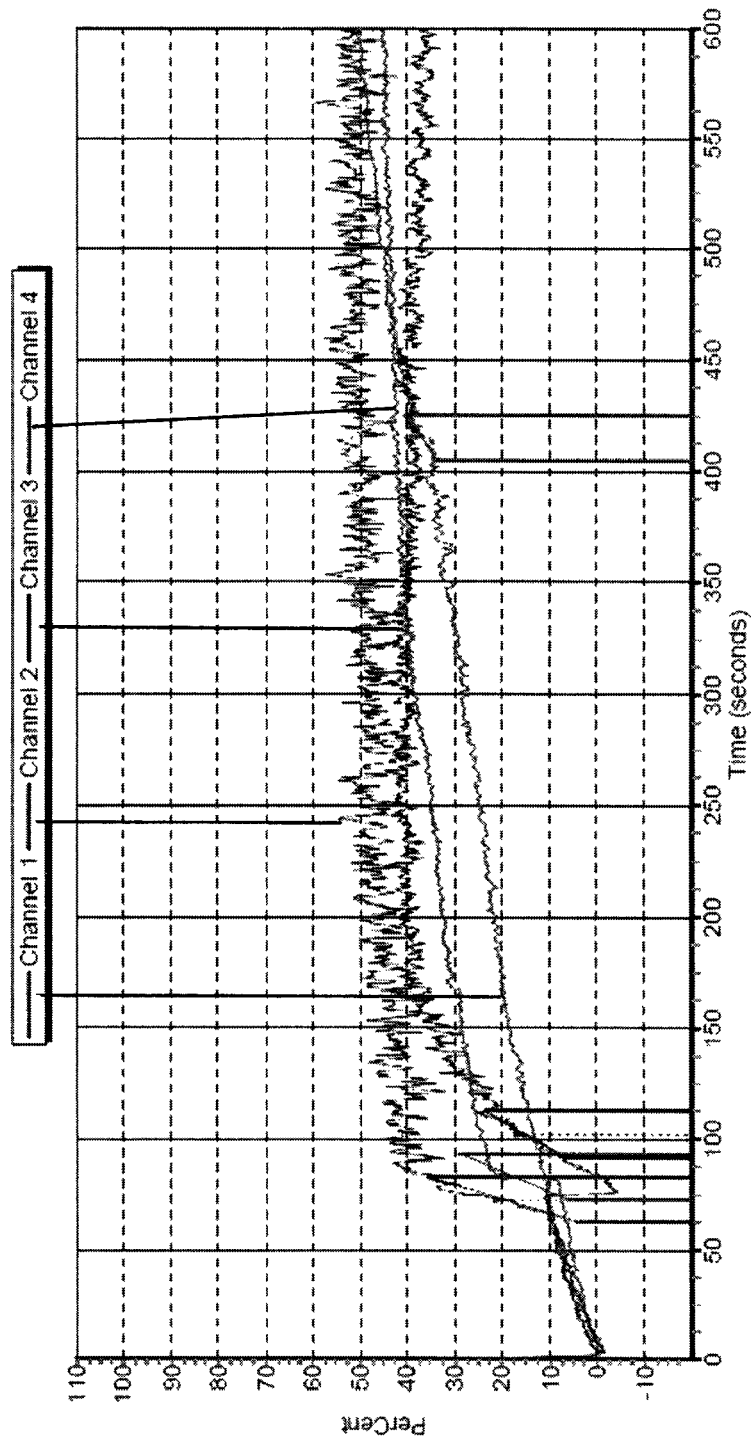
FIG. 2 is a graph depicting the reaction of freeze-dried platelets of the invention with various agonists in plasma.
Figure 3:
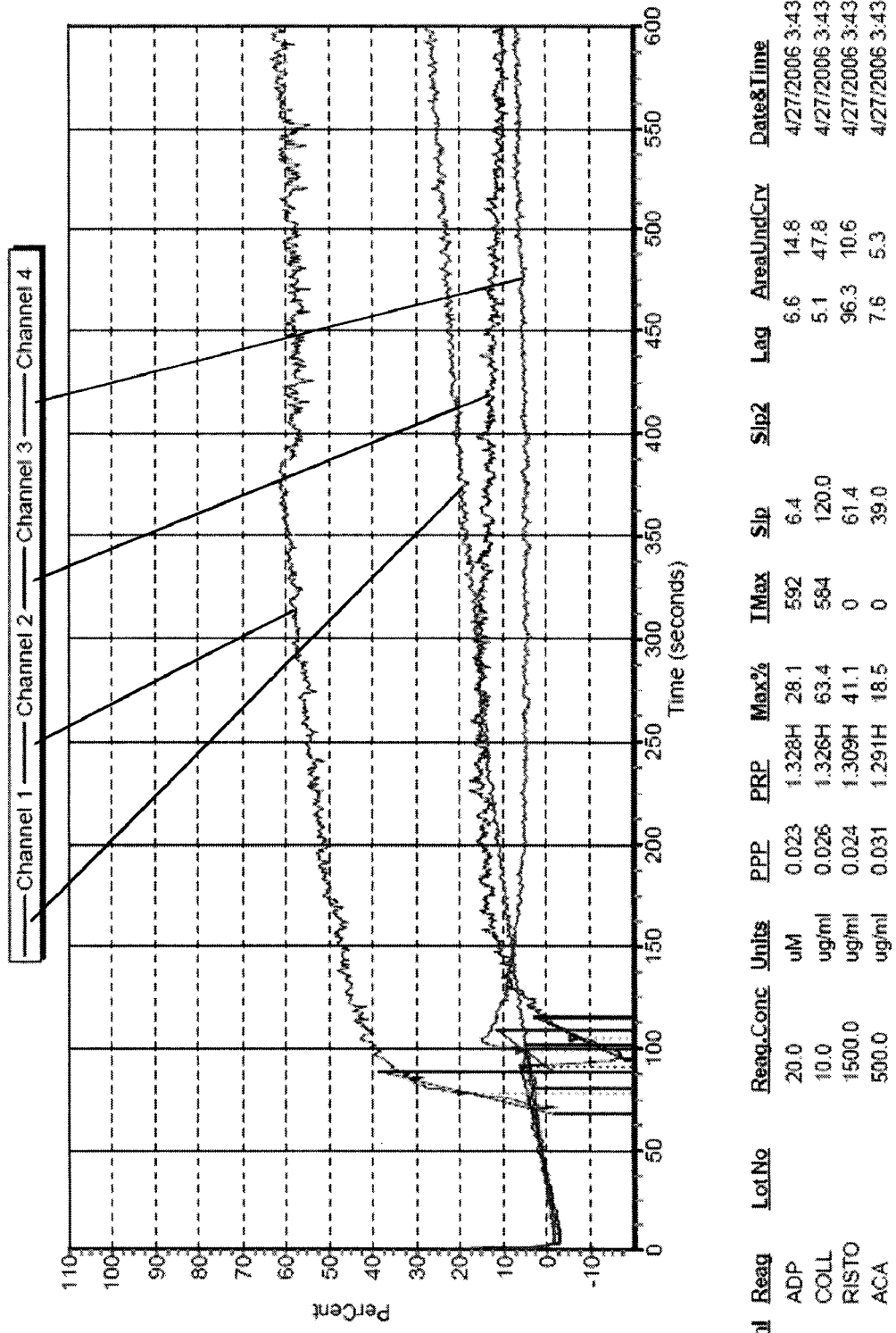
FIG. 3 is a graph depicting the reaction of freeze-dried platelets of the invention with various agonists in a defined buffer.

Aggregation Profile of Freeze-Dried Platelets of the Invention When Processed in Different Buffers In order to determine characteristics of freeze-dried platelets of the invention under different assay conditions, platelets were re-hydrated with deionized water and spun at 1000×g for 5 minutes to pellet. The supernatant was then removed, and the pellet was then brought up in different buffer compositions. As can be seen in FIGS. 2 and 3, the reconstituted platelets proved functional in all buffers tested.

In this analysis, re-hydrated platelets were spun at 1000×g for 5 minutes, and then brought up in George King pooled normal plasma. As shown in FIG. 2, in the AggRam, the platelets were analyzed with no agonist (Channel 1 trace), collagen (Channel 2 trace), ristocetin (Channel 3 trace) and arachidonic acid (Channel 4 trace). While all agonists responded well, producing curves over 50% aggregation, the trace with no agonist showed self aggregation, possibly due to additional damage to the materials related to centrifugation.

For the results shown in FIG. 3, re-hydrated platelets were spun at 1000×g for 5 minutes, and then brought up in Cation-Free HMTA Buffer. As shown in FIG. 3, in the AggRam, the platelets were analyzed with no agonist (Channel 1 trace), collagen (Channel 2 trace), ristocetin (Channel 3 trace) and arachidonic acid (Channel 4 trace). While collagen produced a very strong aggregation curve (over 60% aggregation), ristocetin showed minimal aggregation, and arachidonic acid showed a minimal response.

These results indicate that freeze-dried platelets according to the invention produce the strongest aggregation responses when combined in a 1:1 ratio with pooled normal plasma in the analysis cuvette. The platelets have been combined in a cuvette with HMTA buffer and saline, showing less strong results.

Example 6

Stability of Freeze-Dried Platelets

Figure 4:
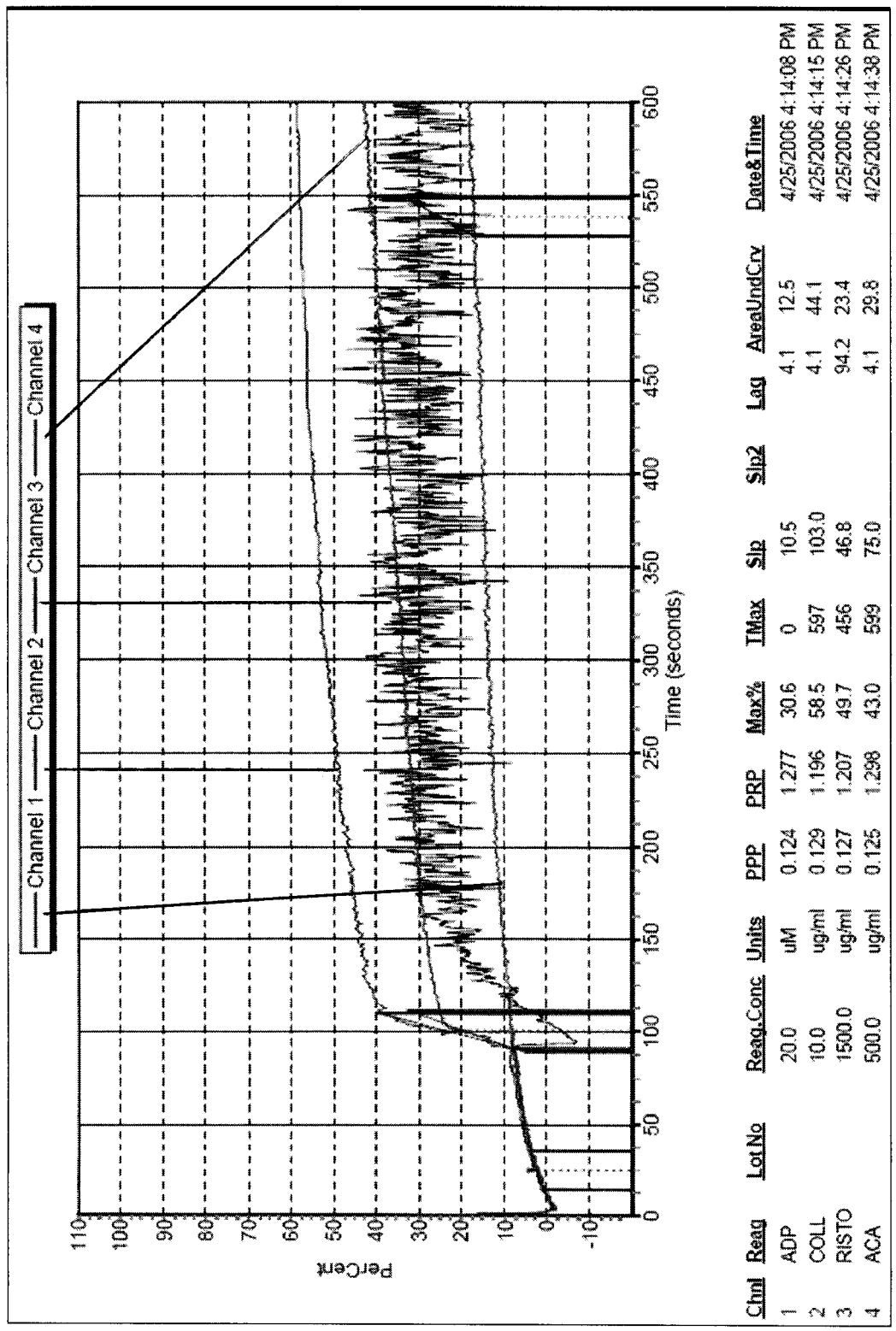
FIG. 4 is a graph depicting the reaction profile of freeze-dried platelets of the invention with various agonists after storage for less than one day.
Figure 5:
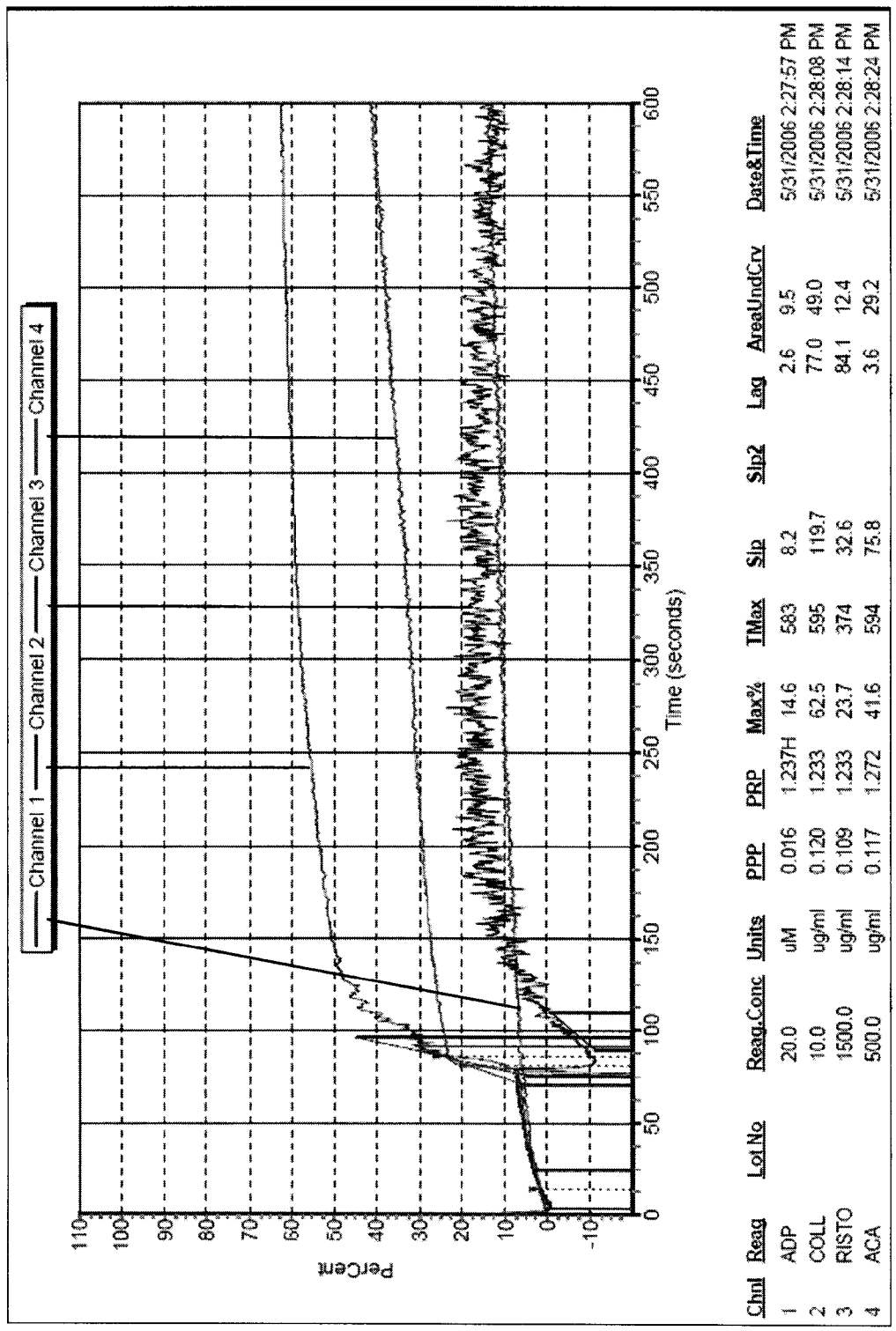
FIG. 5 is a graph depicting the reaction profile of freeze-dried platelets of the invention with various agonists after storage for 36 days.

Experiments were performed to determine the shelf-life of freeze-dried platelets of the present invention. Results presented in FIGS. 4 and 5 indicate that the platelets are stable at room temperature in a dry state for at least 36 days. More specifically, an experiment was performed as described above in Example 4 with the following alteration: freeze-dried samples that were used were 36 day old samples that had been kept at room temperature. What is showed here is that the freeze-dried platelets, when kept at room temperature, retained bio-function longer for up to 36 days or more. This result supports a conclusion that the freeze-dried platelets of the invention have a shelf-life of 36 days or more at room temperature.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

The invention claimed is:

1. A freeze-dried platelet composition comprising platelets, cryoprecipitate or a fraction thereof, polysucrose and trehalose made by the process of:
    obtaining fresh platelets;
    incubating the platelets in DMSO;
    isolating the platelets by centrifugation;
    resuspending the platelets in a loading buffer which comprises trehalose and ethanol thereby forming a first mixture;
    incubating the first mixture;
    mixing cryoprecipitate or a fraction thereof and polysucrose with the first mixture, thereby forming a second mixture; and
    lyophilizing the second mixture to form a freeze dried composition comprising platelets, cryoprecipitate or a fraction thereof, polysucrose and trehalose.

2. The freeze-dried platelet composition of claim 1, wherein the cryoprecipitate or fraction thereof comprises fibrinogen.

3. The freeze-dried platelets of claim 1, wherein the freeze-dried platelets are used as a control reagent.

4. A composition comprising the freeze-dried platelets of claim 1, further comprising one or more biologically tolerable substances.

5. A kit comprising the freeze-dried platelets of claim 1 and further comprising at least one substance that affects the blood clotting system.

6. The kit of claim 5, wherein the substance is a drug.

7. The kit of claim 6, wherein the drug has anti-platelet activity.

8. The kit of claim 6, wherein the drug reduces the ability of a patient's blood to clot.

9. The kit of claim 6, comprising multiple containers containing the freeze-dried platelets.

10. The kit of claim 6, comprising multiple containers containing two or more different substances.

11. A method of determining the blood clotting capability of a sample comprising blood or a blood component, said method comprising:
   combining fresh blood or a blood component with the platelets of claim 1; and
   assaying the mixture of fresh blood or a blood component and the platelets of claim 1 for one or more biological or biochemical functions indicative of one or more blood clotting functions.

12. The method of claim 11, wherein the method is a method of diagnosing a disease or disorder of the blood clotting system.

13. The method of claim 11, wherein the freeze-dried platelets are obtained from a patient having, or suspected of having, a defect in his blood clotting system.

14. The method of claim 11, wherein the fresh blood or blood component is obtained from a patient having, or suspected of having, a defect in his blood clotting system.

15. The method of claim 11, wherein the method is a method of monitoring the progression of a disease or disorder of the blood clotting system.

16. The method of claim 11, which is a method of monitoring the effects of a treatment regimen for a patient on the blood clotting system of that patient.

17. A method of making a freeze-dried platelet composition comprising platelets, cryoprecipitate or a fraction thereof, polysucrose and trehalose comprising:
   obtaining fresh platelets;
   incubating the platelets in DMSO;
   isolating the platelets by centrifugation;
   resuspending the platelets in a loading buffer which comprises trehalose and ethanol thereby forming a first mixture;
   incubating the first mixture;
   mixing cryoprecipitate or a fraction thereof and polysucrose with the first mixture, thereby forming a second mixture; and
   lyophilizing the second mixture to form a freeze-dried composition comprising platelets, cryoprecipitate or a fraction thereof, polysucrose and trehalose.

18. The method of claim 17, wherein the cryoprecipitate or fraction thereof comprises fibrinogen.

19. A rehydrated platelet composition comprising platelets, cryoprecipitate or a fraction thereof, polysucrose and trehalose made by the process of:
   obtaining fresh platelets;
   incubating the platelets in DMSO;
   isolating the platelets by centrifugation;
   resuspending the platelets in a loading buffer which comprises trehalose and ethanol thereby forming a first mixture;
   incubating the first mixture;
   mixing cryoprecipitate or a fraction thereof and polysucrose with the first mixture, thereby forming a second mixture;
   lyophilizing the second mixture to form a freeze-dried composition comprising platelets, cryoprecipitate or a fraction thereof, polysucrose and trehalose; and
   rehydrating the freeze-dried composition.

* * * * *